United States Patent [19]

Menegazzi

[11] Patent Number: 5,732,203
[45] Date of Patent: Mar. 24, 1998

[54] PROCESS FOR RESTORING THE INNER VOLUMES OF A SOLID WITH A VIEW TO COMPUTATIONS AND ASSOCIATED APPLICATION

[75] Inventor: Pascal Menegazzi, Rueil Malmaison, France

[73] Assignee: Institut Francais du Petrole, Rueil-Malmaison, France

[21] Appl. No.: 854,726

[22] Filed: May 12, 1997

Related U.S. Application Data

[63] Continuation of Ser. No. 595,507, Feb. 1, 1996, abandoned, which is a continuation of Ser. No. 174,282, Dec. 28, 1993, abandoned.

[30] Foreign Application Priority Data

Dec. 29, 1992 [FR] France ................ 92/15985

[51] Int. Cl.$^6$ .................................................. G06F 15/00
[52] U.S. Cl. ........................................................ 395/120
[58] Field of Search ............................ 395/120, 124, 395/118, 119, 129; 345/118

[56] References Cited

U.S. PATENT DOCUMENTS

| | | |
|---|---|---|
| 4,879,652 | 11/1989 | Nowak ............................ 364/413.18 |
| 4,969,110 | 11/1990 | Little et al. ............................ 364/550 |
| 5,178,148 | 1/1993 | Lacoste et al. ...................... 128/660.03 |
| 5,184,733 | 2/1993 | Arnarson et al. ........................ 209/585 |
| 5,267,018 | 11/1993 | Kauppinen ............................ 356/379 |
| 5,351,725 | 10/1994 | Suthergreen et al. ........................ 141/1 |
| 5,583,973 | 12/1996 | DeLusi et al. ............................ 395/120 |

FOREIGN PATENT DOCUMENTS 3340024  5/1985  Germany.

OTHER PUBLICATIONS

Computer Vision, Graphics, and Image Processing, vol. 44, No. 1, Oct., 1988, pp. 1–29 J.-D. Boissonnat "Shape Reconstruction from Planar Cross Sections".

*Primary Examiner*—Phu K. Nguyen
*Attorney, Agent, or Firm*—Antonelli, Terry, Stout, & Kraus, LLP

[57] ABSTRACT

The reconstitution of volumes located inside a solid for carrying out computations relative to the volume is disclosed. The process comprises producing digitized images of a plurality of parallel cross-sections of the solid surrounding the volume, processing the digitized images to digitally create a contour of the volume, and digitally processing the contour of the volume so that the contour may be exploited for application. An application of the process is for example reconstitution of a cooling circuit of a cylinder head of an internal-combustion engine.

12 Claims, 4 Drawing Sheets

PROCESS FOR RESTORING THE INNER VOLUMES OF A SOLID WITH A VIEW TO COMPUTATIONS AND ASSOCIATED APPLICATION

This is a continuation of application Ser. No. 08/595,507, filed Feb. 1, 1996, now abandoned, which is a continuation application of U.S. Ser. No. 08/174,282 filed on Dec. 28, 1993, now abandoned.

BACKGROUND OF THE INVENTION

1. Field of the Invention

The present invention relates to the reconstitution of volumes located inside a solid, which may be concealed or difficult to access, having a shape which must be accurately known and on which digital computations are to be performed.

2. Description of the Prior Art

It is well-known to precisely determine physical quantities such as for example, of simple shapes located inside a solid element.

These physical quantities cannot be measured directly with conventional instruments, such as measuring rules, slide calipers, protractors, etc,. Processes utilizing for example ultrasound or the absorption of a given radiation are used to determine the shape and/or the dimension of the volume to be analyzed.

According to planned applications, it is possible to determine either numerical values relative to the volumes, or shapes or contours of the concealed volumes.

Medical imagery for example often tries to restore contours according to planes. Scanners and equipment based on nuclear magnetic resonance for example allow the shapes of various human organs (brain, liver . . . ) to be displayed according to cross-sections, but they generally are not enable to go on farther into an analysis of these organs.

It is well-known to restore, by means of mathematical methods, all or part of the geometric characteristics of any volume which are known in advance.

Some geometric characteristics of the shape to be restored are the inputs of a program which determines automatically the general shape. These programs are called "meshing" programs because they define the geometry from juxtaposed meshes (or polygons) which are also called a "mesh pattern". Mesh patterns may be two-dimensional or there-dimensional.

Finally, it is well-known to carry out various computations from mesh patterns. Finite element or finite difference computation algorithms are commonly used to this end.

However, as already mentioned, these computation methods require a prior knowledge of the geometries of the elements on which computations are achieved, and notably the geometries of concealed volumes.

This prior knowledge of the geometries of the elements is often difficult to obtain, particularly when precision computations are to be carried out.

Furthermore, the data, i.e. the geometries of the volumes in question, are generally input point by point, which requires substantial implementation time.

Under the most favourable conditions, the most significant points of the geometry have to be inputted, and an automatic mesh pattern may then generate the characteristics of the other mesh points by interpolation. This type of process does of course not allow complex geometries to be processed.

SUMMARY OF THE INVENTION

The object of the present invention is to provide a remedy for the drawbacks mentioned above.

The invention particularly allows complex volumes to be accurately restored and permits digital computations to be made from such volumes.

The present application is advantageously, but not exclusively, applied to concealed volumes located inside a solid.

It is therefore possible to restore and to analyze volumes whose geometry is not precisely known. The invention allows for example computations to be performed on pipes embedded in a solid for displaying any wear or a layer formed during operation. It is thus possible to precisely restore the shape of inner pipes after such a pipe has been used for a certain time, and to carry out computations directly from these concealed and a prior unknown volumes. The invention is here applied to the field of non-destructive testing.

The main advantage of the invention is that it allows complex volumes to be processed with considerable less time when compared with the prior art.

In fact, as contained in the description above, when complex volumes are to be subjected to scientific computations, it takes a long time to integrate their geometry into storage in the computer memory.

The present invention allows a nearly automatic fast acquisition of data representing any geometry.

The main objects and advantages which have been mentioned above are obtained by means of an automatic reconstitution process for volumes located notably inside solids, in order to carry out computations relating to the volumes.

According to the invention, the process comprises the following stages:

obtaining digitized images of several parallel cross-sections of the space surrounding the volume;

processing the digitized images to create a digital contour of the volume; and digitally processing the contour.

More precisely the processing of the digital images to create a digital contour comprises:

determining the contour of the volume of each digitized image;

approximating with polygons the determined contours;

locating vertices of the polygons; and creating, from data representing the vertices, a surface mesh pattern approximating a real contour of the volume.

In other words, the invention according to the last stage of digital processing comprises using an algorithm allowing a volume mesh pattern formed from polygons of the object to be created form the surface mesh pattern formed during the preceding stage of processing the digitized images to create a digital contour.

This volume mesh pattern is used thereafter for digital computations.

According to a preferred embodiment of the invention, the polygons created are mainly triangles and the volume elements are mainly tetrahedra.

The computation algorithms may be of the non-structured finite element or finite volume type.

According to one embodiment of the invention, the digitized images are obtained by means of a scanner which allows the acquisition and then the digitizing of each cross-section.

Without departing from the scope of the invention, the digitized images may be obtained from files (CAD) consisting of mathematical entities processed to obtain data on each pixel of the digitized images.

According to another aspect thereof, the process according to the invention defined above is applied to the reconstitution of an inner cooling circuit of a cylinder head of an internal-combustion engine. The cylinder head may be made from aluminum.

BRIEF DESCRIPTION OF THE DRAWINGS

Other features and advantages of the invention will be clear from reading the description hereafter, given by way of non limitative examples, with reference to the accompanying drawings in which.

BRIEF DESCRIPTION OF THE PREFERRED EMBODIMENTS

Figure 1:
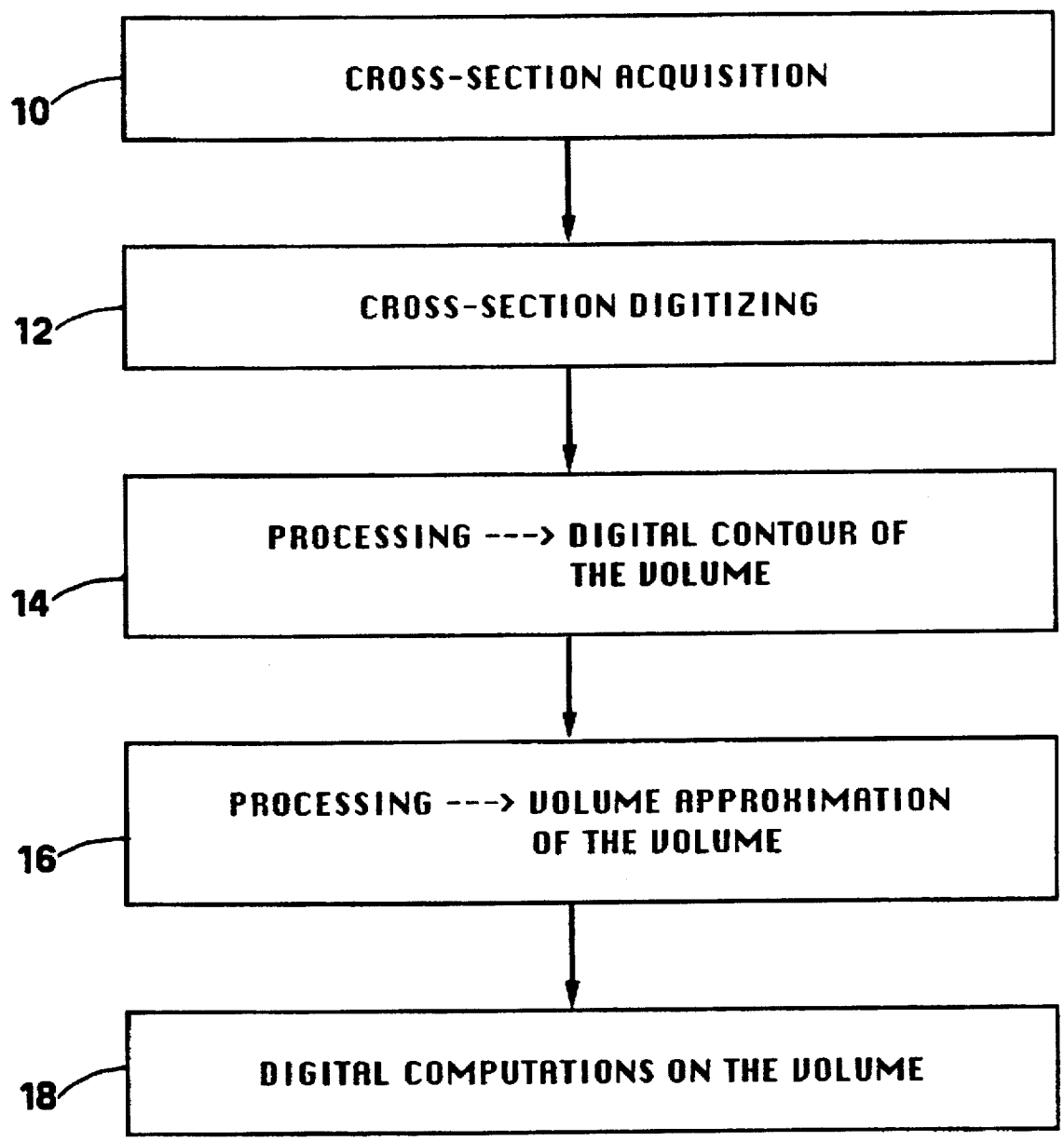
FIG. 1 is a flow chart showing the main operations performed during the implementation of a process according to the invention.

The main stages of the process according to the invention are illustrated in FIG. 1.

The first stage is the obtaining of parallel cross-sections of the space surrounding the volume. The distance between each cross-section is preferably constant and is defined as a function of the planned application. The distance between the section is selected so that geometry variations are easily detected. A scanner known in the art may be used to obtain the sections.

Figure 4A:
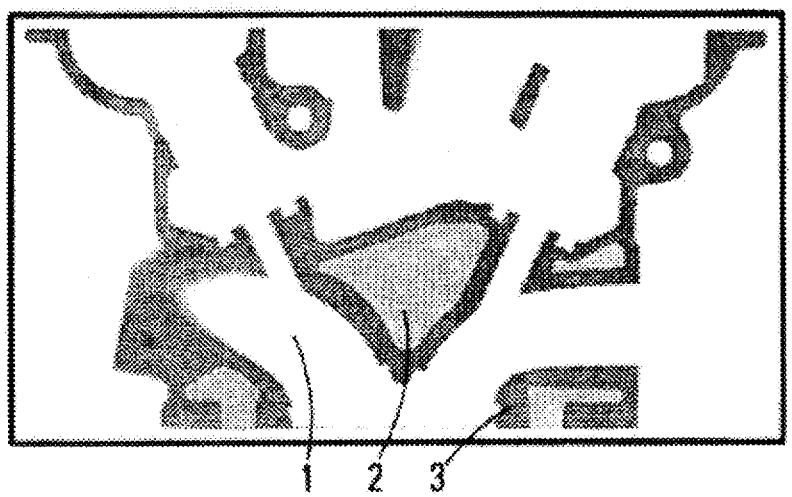
FIGS. 4A, 4B and 4C each show a tomogram obtained with a scanner.
Figure 4B:
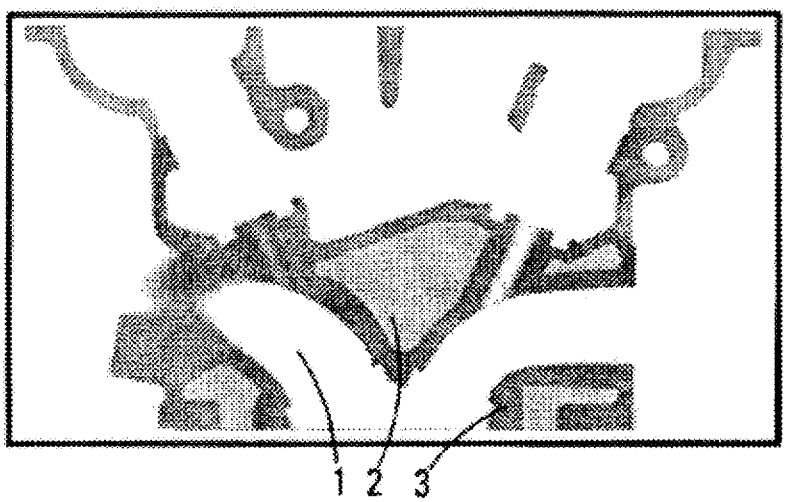
Figure 4C:
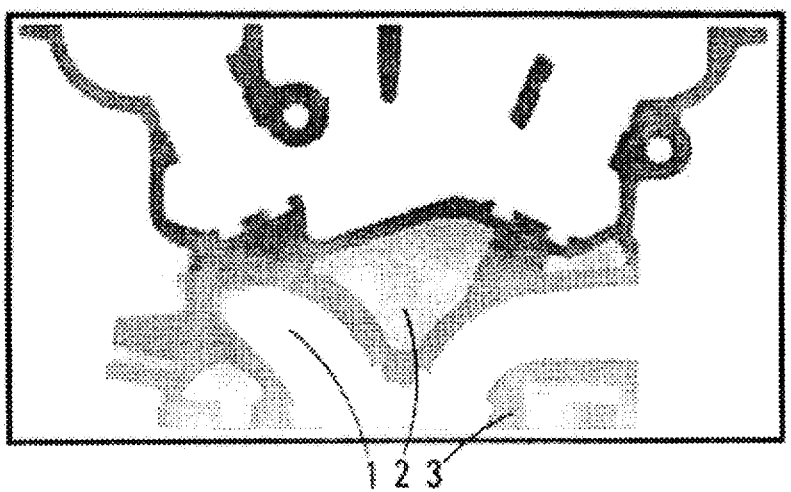

A series of cross-sections such as those for example shown in FIGS. 4A, 4B and 4C are thus obtained. These sections may be digitized by the scanner or by a computer as indicated at stage 12.

Without departing from the scope of the invention, it is also possible to obtain digitized sections from files, for example from CAD files consisting of mathematical entities. These mathematical entities are processed by specific software intended for converting them into data linked to each pixel of the entities. A pixel is an elementary unit of a digital image.

Figure 2:
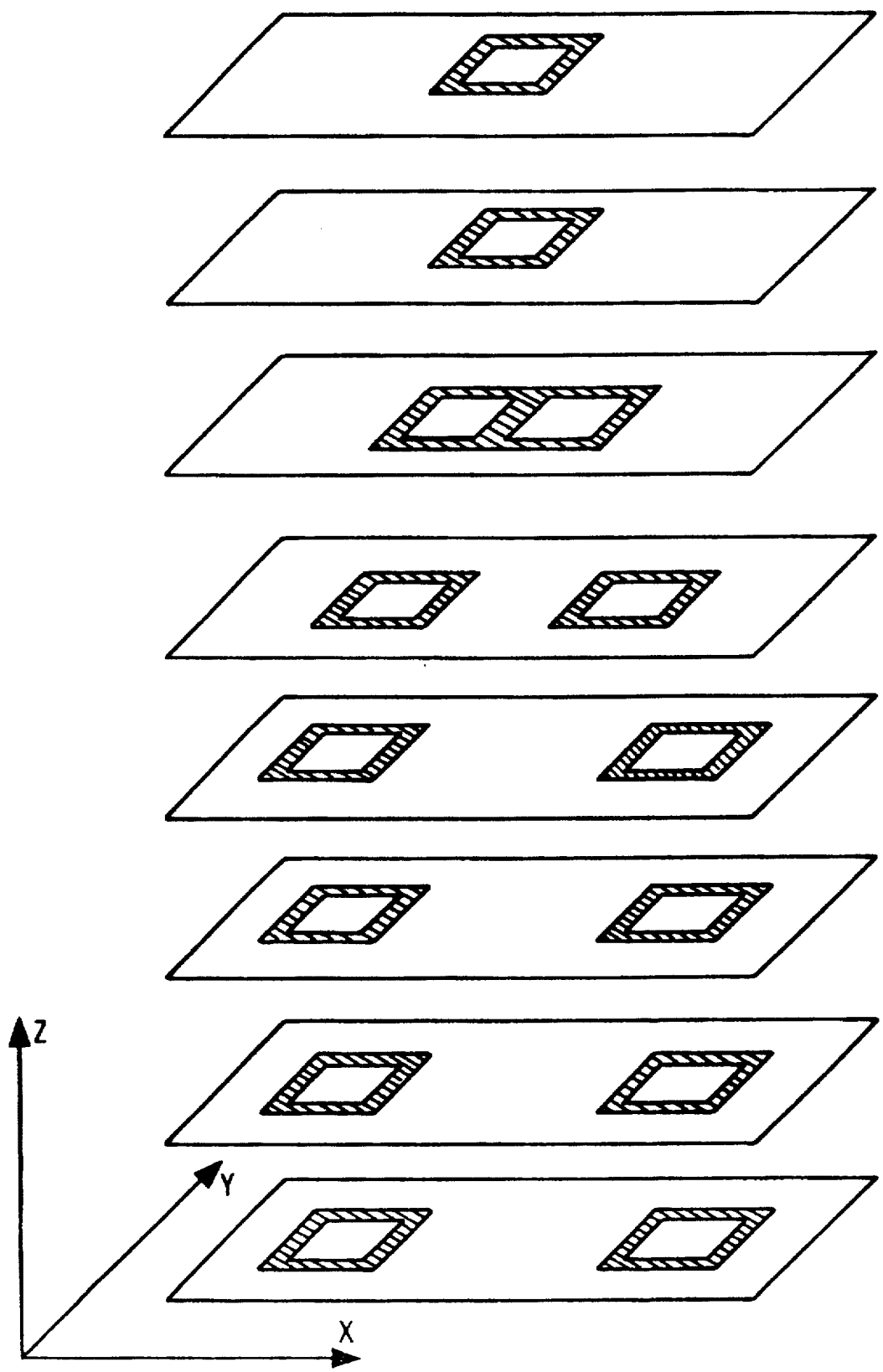
FIG. 2 diagrammatically shows various parallel cross-sections of a volume to be restored.

FIG. 2 diagrammatically shows an example of all of the cross-sections which may be obtained for a given volume.

In all cases, during stage 14, the digitized data gathered in the files are processed by specific software which creates a mesh pattern or contour of polygons, called a surface contour, of the volume to be restored.

More precisely stage 14 comprises the following steps;

locating the contour of the volume of each cross-section;

approximating each contour using polygons;

optionally modifying or rectifying the contour;

locating certain vertices (or nodes) of the polygons for assigning particular physical characteristics, also called boundary conditions, thereto; and creating a surface representation of the volume in the form of a volume contour, consisting of juxtapose polygons which approximates the real volume contour.

In other words, at the end of stage 14, a mesh pattern of polygons defining an outer contour of the volume is obtained.

Stage 16 creates a volume mesh pattern of the volume, i.e. to obtain a three-dimensional digital approximation of the volume. In other words, the volume to be restored is approximated by a set of digitally defined volumes juxtaposed with respect to each other. An automatic meshing algorithm such as the VORONOI algorithm is used to create a three-dimensional mesh pattern which may be interfaced with digital computing software.

Stage 18 carries out digital computations from data relative to the volume mesh pattern.

Figure 3:
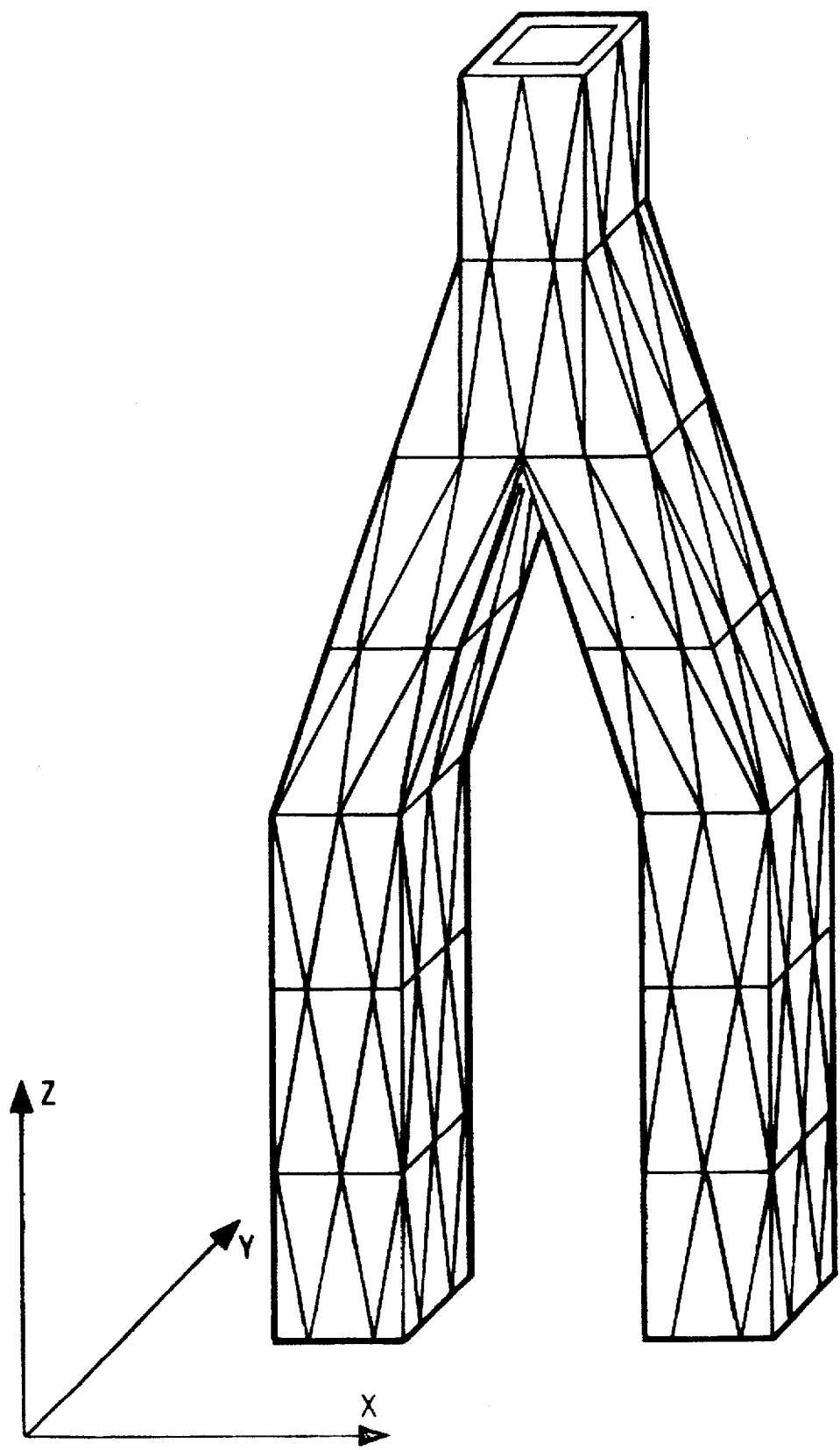
FIG. 3 diagrammatically shows a volume restored according the invention.

FIG. 3 shown in a simplified way an example of a volume defined by juxtaposed polygons. The elementary volumes (or volume meshes) are tetrahedra and the surface polygons are triangles. Other types of surface polygons and elementary volumes may be processed without departing from the scope of the present invention.

A particular application example of the process according to the invention is described hereunder.

The methodology described above has been used to describe and carry out computations of inner cooling circuits of a cylinder head of an internal-combustion engine.

The cylinder head according to this example is made from aluminum, a material compatible with the capability of the scanner which is used. In fact, metals having too high an absorption of the X-radiation produced by the scanner cannot be used. Aluminum, consisting of light constituents, allows good performance to obtain a particularly good image quality.

Before the cylinder head is analyzed by the scanner, it is preferably cleared of the parts made of heavy metals for the reasons mentioned above.

In order to distinguish it very clearly from the other surrounding elements (other circuits notably), the volume to be analyzed has been filled with water. Scanner analysis is achieved thereafter by producing successive sectional images.

FIGS. 4A, 4B and 4C show each a tomogram, i.e. a photograph of a sectional image obtained according to the present embodiment example of the invention.

In the present application example of the invention, a cross-section has been achieved every two millimeters, and about 200 cross-sections have been performed. These images are thus digitized, stored and processed according to stages 14 and 16 described above.

In FIGS. 4A, 4B and 4C, the white areas 1 correspond to empty volumes filled with air, the dark grey areas 3 represent the material (the aluminum cylinder head here) and the lighter grey areas 2 correspond to the volume to be analyzed, i.e. the cooling circuit of the cylinder head.

A surface mesh pattern and then a volume mesh pattern of the geometry are thus successively obtained. The volume mesh pattern comprises on the whole over 100 000 nodes from which a computing program may carry out several types of computations. For example, a computing program from the field of fluid mechanics may be used permitting temperatures, flow rates, velocity of flow, etc. to be calculated at the various nodes of the mesh pattern, i.e. in a multitude of points of the structure to be analyzed.

In order to illustrate one of the above-mentioned advantages of the invention, a computation of the type defined above requires about one week of work.

To obtain a substantially comparable result, more or less six months of work are necessary with conventional methods.

Of course, the invention may be used in various other applications other than that which has been briefly described by way of non limitative examples set for above.

I claim:

1. A process for digitally performing computations on a three-dimensional representation of a volume surrounded by a solid comprising:

(a) obtaining digitized images of a plurality of cross sections of the solid containing a fluid and surrounding the volume;

(b) processing the digitized images to create a digital representation of the volume;

(c) digitally performing computations on the digital representation of the volume to produce a computational result which is different form the digital representation of the volume; and (d) performing restoration of the volume with use of the computational result.

2. A process in accordance with claim 1 wherein:

the computational result is obtained from processing the digital representation of the volume with an application of fluid mechanics.

3. A process in accordance with claim 2 wherein the computational result comprises:

at least one of temperature, flow rate through the volume or velocity of flow through the volume.

4. A process in accordance with claim 3 wherein step (b) comprises:

processing the digital images to create a digitally represented contour of the volume within the solid surrounding the volume;

approximating with polygons the digitally represented contour;

locating vertices of the polygons; and creating from a digital representation of the vertices the digital representation of the volume.

5. A process in accordance with claim 4 wherein:

the creating of the digital representation of the volume uses a non-structural finite element type algorithm.

6. A process in accordance with claim 4 wherein:

the creating of the digital representation of the volume uses a non-structured finite volume type algorithm.

7. A process in accordance with claim 2 wherein step (b) comprises:

processing the digital images to create a digitally represented contour of the volume within the solid surrounding the volume;

approximating with polygons the digitally represented contour;

locating vertices of the polygons; and creating from a digital representation of the vertices the digital representation of the volume.

8. A process in accordance with claim 7 wherein:

the creating of the digital representation of the volume uses a non-structural finite element type algorithm.

9. A process in accordance with claim 7 wherein:

the creating of the digital representation of the volume uses a non-structured finite volume type algorithm.

10. A process in accordance with claim 1 wherein step (b) comprises:

processing the digital images to create a digitally represented contour of the volume within the solid surrounding the volume;

approximating with polygons the digitally represented contour;

locating vertices of the polygons; and creating from a digital representation of the vertices the digital representation of the volume.

11. A process in accordance with claim 10 wherein:

the creating of the digital representation of the volume uses a non-structural finite element type algorithm.

12. A process in accordance with claim 10 wherein:

the creating of the digital representation of the volume uses a non-structured finite volume type algorithm.

* * * * *